(12) United States Patent
Forgione et al.

(10) Patent No.: US 6,197,957 B1
(45) Date of Patent: Mar. 6, 2001

(54) PROCESS FOR PREPARING DERIVATIVES OF (HALO)AMINO-1,3,5-TRIAZINES BY CARBONYLATION

(75) Inventors: Peter S. Forgione, Stamford, CT (US); Ram B. Gupta, Bronx, NY (US); Lawrence A. Flood, Norwalk; Donald H. Valentine, Ridgefield, both of CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 08/138,581

(22) Filed: Oct. 15, 1993

(51) Int. Cl.[7] ..................... C07D 251/42; C07D 251/48; C07D 251/54
(52) U.S. Cl. ................. 544/198; 544/194; 544/200; 544/205; 544/207; 544/212
(58) Field of Search .................................. 544/194, 198, 544/200, 207, 205, 212

(56) References Cited

U.S. PATENT DOCUMENTS

| 3,405,156 | 10/1968 | Stern et al. ........................ 260/453 |
| 3,641,092 | 2/1972 | Henry et al. ........................ 260/453 |
| 4,939,213 | 7/1990 | Jacobs, III et al. .................. 525/329 |
| 5,008,435 | 4/1991 | Lob et al. .............................. 560/24 |
| 5,068,424 | 11/1991 | Besenyel et al. .................... 562/870 |
| 5,084,541 | 1/1992 | Jacobs, III et al. .................. 528/45 |
| 5,194,660 | 3/1993 | Leung et al. .......................... 560/24 |

FOREIGN PATENT DOCUMENTS

| 0083 096 | 12/1982 | (EP) ........................................ 125/6 |

OTHER PUBLICATIONS

Chow, Y.L. et.al., "A Novel Catalystic Synthesis of Carbamates by the Oxidative Akoxycarbonylation of Amines in the Presence of Platinum Group Metal and Alkali Metal Halide or Onium Halide," *J. Org. Chem.* 49, pp. 1458–1460 (1984).

P. Giannoccarro, "Palladium Catalysed N,N'-Disbustituted Urea Synthesis by Oxidative Carbonylation of Amines under CO and $O_2$ at Atmospheric Pressure", *Journal of Organanometallic chemistry*, 336, pp. 271–278 (1987).

Davis, C. and M. Kilner, "A Study of Palladium–Catalysed Carbonylation of N–Chloramines," *Journal of Catalysis*, 136, pp. 404–414 (1982).

Saegusa, T. et.al., Carbonate Formation by the Reaction of Cupric Methoxide and Carbon Monoxide, : *Tetrahedron Letters*, 7, pp. 831–833 (1968).

Saegusa, T. et.al., "Carbamoyl Chloride Formation from Chloramine and Carbon Monoxide." *J. Org. Chem*.rbonylation of Amines in the Presence of Palladium and, 36(6), pp. 858–860 (1971).

S–TriaZines and Derivatives, Edwin M. Smolin and L. Rapaport Inter Science Publisher Inc., New York, 1959.*

* cited by examiner

Primary Examiner—Richard L. Raymond
(74) Attorney, Agent, or Firm—Valerie T. Didamo; Claire M. Schultz; Liza Negron

(57) ABSTRACT

Provided is a process for preparing carbonylated derivatives of amino- and haloamino-1,3,5-triazines by contacting the 1,3,5-triazine, carbon monoxide and a metal catalyst system containing a metal promoter for promoting carbonylation, at a temperature carbon monoxide pressure and length of time sufficient to carbonylate at least a portion of the amino and/or haloamino groups of the 1,3,5-triazine. The product resulting from contacting these components is an isocyanate functional 1,3,5-triazine; however, the carbamate functional derivative can be readily produced by contacting these components in the further presence of a hydroxy compound, or by post-reacting the isocyanate functional product with such hydroxy compound.

37 Claims, No Drawings

PROCESS FOR PREPARING DERIVATIVES OF (HALO)AMINO-1,3,5-TRIAZINES BY CARBONYLATION

BACKGROUND OF THE INVENTION

1. Field of the Invention

This invention relates to the preparation of isocyanate and carbamate functional derivatives of optionally halogenated amino-1,3,5-triazines via carbonylation using carbon monoxide and a metal promoter for promoting carbonylation.

2. Description of Related Art

Various derivatives of (halo)amino-1,3,5-triazines are described in the literature as being utilized in a wide variety of fields. An important use of certain of these derivatives, such as methoxymethyl derivatives of melamine and guanamines, is as crosslinkers and/or reactive modifiers in curable compositions which contain resins having active hydrogen groups. While these methoxymethyl derivatives provide excellent results in a number of aspects, they also have the disadvantage of releasing formaldehyde as a volatile by-product under curing conditions. It has long been a desire of industry to find acceptable alternatives which do not emit formaldehyde upon cure.

One such alternative that has shown great promise is carbamate functional 1,3,5-triazines which are disclosed in commonly owned U.S. Pat. No. 4,939,213, U.S. Pat. No. 5,084,541, U.S. application Ser. No. 07/968,871, now U.S. Pat. No. 5,288,865 (filed Oct. 30, 1992, which is a continuation-in-part of U.S. application Ser. No. 07/793,077, filed Nov. 15, 1991 and now abandoned), U.S. application Ser. No. 07/998,313, now U.S. Pat. No. 5,571,103 (filed Dec. 29, 1992) and U.S. application Ser. No. 08/061,905, now abandoned (filed May 14, 1993), all of which are hereby incorporated by reference herein as if fully set forth. Specifically, the carbamate functional 1,3,5-triazines disclosed in these references have been found to be particularly useful as crosslinkers in coating compositions based upon hydroxy functional resins, with the cured coatings possessing a wide range of desirable properties.

One hinderance to the commercial use of these carbamate functional 1,3,5-triazines has been that the known preparation methods can be somewhat cumbersome, difficult and expensive. For example, in previously incorporated U.S. Pat. No. 4,939,213 and U.S. Pat. No. 5,084,541, the 1,3,5-triazine carbamates are produced in a two-step process by first reacting an amino-1,3,5-triazine with oxalyl chloride to produce an isocyanate functional intermediate, then reacting this intermediate with an alcohol. Further, in previously incorporated U.S. application Ser. No. 07/968,871, now U.S. Pat. No. 5,288,865, carbamate functional 1,3,5-triazines are produced in a one-step process by reacting a haloamino-1,3,5-triazine with an acid halide. The primary disadvantages to these process include the use of certain costly halogenated starting materials, production of substantial amounts of halogenated by-products, and low ultimate yield of the desired products.

Many of the problems with these processes have been solved by the process disclosed in previously incorporated U.S. application Ser. No. 08/061,905, wherein carbamate functional 1,3,5-triazines are produced by reacting an at least bis-amino 1,3,5-triazine with an acyclic organic carbonate in the presence of a strong base. Disadvantages to this process include, for example, that the strong base must be neutralized to remove it from the end product, and that certain aspects of the reaction must be carefully controlled in order to avoid color in the end product.

It has now been surprisingly discovered after extensive research that isocyanate functional 1,3,5-triazines can be produced without many of the disadvantages of the prior art processes by the carbonylation of (halo)amino-1,3,5-triazines with carbon monoxide in the presence of a metal promoter for promoting carbonylation. These isocyanate functional 1,3,5-triazines may be readily converted to the carbamate counterparts either by carrying out the carbonylation in the presence of a hydroxy compound or by adding the hydroxy compound to the isocyanate functional 1,3,5-triazine without isolating it.

It should be noted that it is generically known to obtain isocyanates via the carbonylation of (halo)amines, and carbamates by the further reaction of those isocyanates with hydroxy compounds. As representative disclosures, reference can be made to the following, which are incorporated by reference herein as if fully set forth:

Saegusa, T. et al., "Carbonate Formation by the Reaction of Cupric Methoxide and Carbon Monoxide," *Tetrahedron Letters*, 7, pp. 831–833 (1968);

Saegusa, T. et al., "Carbamoyl Chloride Formation from Chloroamine and Carbon Monoxide," *J. Org. Chem.*, 36(6), pp. 858–860 (1971);

Fukuoka, S. et al., "A Novel Catalytic Synthesis of Carbamates by Oxidative Alkoxycarbonylation of Amines in the Presence of Palladium and Iodide," *J. Chem. Soc., Chem. Commun.*, pp. 399–400 (1984);

Chow, Y. L. et al., "A Novel Catalytic Synthesis of Carbamates by the Oxidative Alkoxycarbonylation of Amines in the Presence of Platinum Group Metal and Alkali Metal Halide or Onium Halide," *J. Org. Chem.*, 49, pp. 1458–1460 (1984);

P. Giannoccarro, "Palladium Catalysed N,N'-Disubstituted Urea Synthesis by Oxidative Carbonylation of Amines under CO and $O_2$ at Atmospheric Pressure," *Journal of Organometallic Chemistry*, 336, pp. 271–278 (1987);

Davies, C. and M. Kilner, "A Study of Palladium-Catalysed Carbonylation of N-Chloroamines," *Journal of Catalysis*, 136, pp. 403–414 (1992);

U.S. Pat. No. 3,405,156; U.S. Pat. No. 3,641,092; EP-A-0083096; U.S. Pat. No. 5,008,435; U.S. Pat. No. 5,068,424 and U.S. Pat. No. 5,194,660.

This chemistry, however, has apparently not been applied to (halo)amino-1,3,5-triazines. Indeed, one of ordinary skill in the art could not reasonably expect success in doing so, since it is well-known to the skilled person that the amine functionality of amino-1,3,5-triazines (such as the amine functionality of melamines and guanamines) is not equivalent to the other types of typical amine functionality. Melamines and guanamines are among the least reactive of the "amines" and the most difficult to functionalize, and their behavior cannot normally be correlated to that of other known amines, even structurally similar amines such as pyrimidines.

For example, most "typical" amines are highly reactive with acid halides. In a publication by E. M. Smolin and L. Rappaport entitled "S-Triazines and Derivatives," Interscience Publishers Inc., New York, page 333 (1959), it is reported that attempts to react an acid halide with the amino group on a 1,3,5-triazine such as melamine were not successful. Further, attempts to functionalize amino-1,3,5-triazines often results in substitution at the nitrogen on the triazine ring. For example, it is known that the reaction of melamine with alkyl halides, such as allyl chloride, results in alkyl substitution at the nitrogen on the triazine ring resulting in isomelamine derivatives.

In light of the known literature, therefore, it is in fact quite surprising that amino- and haloamine-1,3,5-triazines can be carbonylated under the conditions as described below.

SUMMARY OF THE INVENTION

In accordance with the present invention, there is provided a process for preparing carbonylated derivatives of (halo)amino-1,3,5-triazines, comprising the step of contacting (a) a (halo)amino group-containing 1,3,5-triazine represented by the formula:

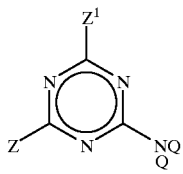

wherein each Q is independently selected from the group consisting of hydrogen and halogen, Z is selected from the group consisting of a group represented by the formula —N(Q$^1$)$_2$, and a group represented by the formula:

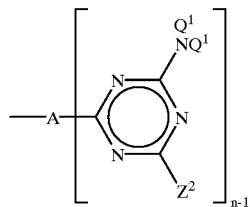

$Z^1$ is selected from the group consisting of hydrogen, hydrocarbyl, a group represented by the formula —N(Q$^1$)$_2$, and a group represented by the formula:

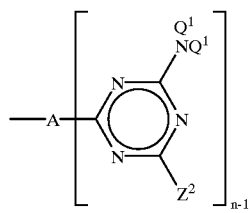

A is an n-functional anchor, n is at least 2, each $Q^1$ is independently selected from the group consisting of hydrogen, halogen, a hydrocarbyl and a hydrocarbyloxy hydrocarbyl, and each $Z^2$ is independently selected from the group consisting of hydrogen, hydrocarbyl and a group represented by the formula —N(Q$^1$)$_2$;

(b) carbon monoxide; and (c) a metal catalyst system containing a metal promoter for promoting carbonylation;

at a temperature, carbon monoxide pressure, and length of time sufficient to carbonylate at least a portion of the (halo)amino groups of the 1,3,5-triazine.

When the 1,3,5-triazine contains an amino group or a mixed haloamino group to be carbonylated, it is preferred that an oxidant system be present in an amount sufficient to restore the metal promoter to a promotively effective oxidation state. When the 1,3,5-triazine contains a mixed haloamino or fully haloamino group to be carbonylated, it is preferred that a hydrogen halide acceptor be present in an amount sufficient to neutralize the hydrohalide by-product of the carbonylation.

The 1,3,5-triazine carbonylated product produced by contacting (a), (b), and (c) is an isocyanate functional 1,3,5-triazine. A carbamate functional 1,3,5-triazine derivative, however, can readily be produced by one of two routes—(i) reacting components (a), (b), (c) in the presence of a hydroxy compound, or (ii) by post-reacting the isocyanate 1,3,5-triazine derivative with such a hydroxy compound.

As indicated above, the advantages of the present process include, for example:

(1) the present process does not require the use of a strong base;

(2) the present process does not require the use of environmentally undesirable formaldehyde;

(3) the present process does not require the use of costly halogenated reagents such as oxalyl chloride; and (4) if a carbamate functional derivative is desired, the present process does not require the handling or isolation of an isocyanate intermediate.

These and other features and advantages of the present invention will be more readily understood by those of ordinary skill in the art from a reading of the following detailed description.

DETAILED DESCRIPTION OF THE PREFERRED EMBODIMENTS

As mentioned above, the present invention is a process for preparing carbonylated 1,3,5-triazine derivatives via the carbonylation of (halo)amino group-containing 1,3,5-triazines.

The term "(halo)amino group-containing 1,3,5-triazine," in the context of the present invention, refers to 1,3,5-triazine compounds containing at least one of an amino group (—NH$_2$), mixed haloamino group (—NH(Hal)) and/or fully haloamino group (—N(Hal)$_2$) as a substituent attached to the 1,3,5-triazine core.

The term "carbonylation," in the context of the present invention, refers to a chemical reaction by which a carbonyl (C═O) group is introduced into at least a portion of the (halo)amino groups of the 1,3,5-triazine starting material. Without being bound by theory, it is believed that carbonylation takes place only at the sites of the (halo)amino groups of the 1,3,5-triazines. The actual mechanism, however, is unclear, particularly when the reaction takes place in the presence of a hydroxy compound with the resulting formation of carbamate functional 1,3,5-triazines.

In view of the meaning of carbonylation, a "carbonylated product" or a "carbonylated derivative," in the context of the present invention, refers to a 1,3,5-triazine product with a substituent containing a carbonyl (C═O) group which has been introduced via carbonylation. For example, the fully carbonylated product of melamine (2,4,6-triisocyanato-1,3, 5-triazine) is a carbonylated product in the context of the present invention, as are the carbamate derivatives thereof (such as 2,4,6-tris-(methoxycarbonylamino)-1,3,5-triazine). Another related example of a carbonylated product in the context of the present invention is 2,4,6-tris-(chlorocarbonylamino)-1,3,5-triazine.

The process of the present invention includes the use of carbon monoxide and a metal catalyst system containing a metal promoter for promoting carbonylation of the (halo) amino groups for converting them to an isocyanate. When the process is carried out in the presence of a hydroxy compound such as an alcohol or a phenol, or when a hydroxy compound is added subsequent to the formation of the isocyanate functional 1,3,5-triazine, there is obtained a carbamate functional 1,3,5-triazine. When the carbamate functional 1,3,5-triazine is at least bis-functional, there is obtained a crosslinking agent and/or reactive modifier usable with polyfunctional active hydrogen containing resins, such as hydroxyfunctional acrylic or polyester resins, for producing curable compositions which have utility in coatings, adhesives, molding, and other applications, as disclosed in the previously incorporated commonly owned references.

The 1,3,5-Triazine Starting Material

As indicated above, the 1,3,5-triazine suitable for use in the process of the present invention is a (halo)amino group-containing 1,3,5-triazine represented by the formula:

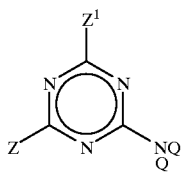

wherein each Q is independently selected from the group consisting of hydrogen and halogen, Z is selected from the group consisting of a group represented by the formula —N(Q$^1$)$_2$, and a group represented by the formula:

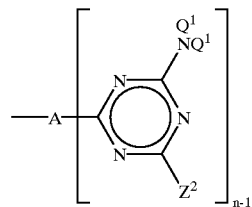

Z$^1$ is selected from the group consisting of hydrogen, hydrocarbyl, a group represented by the formula —N(Q$^1$)$_2$, and a group represented by the formula:

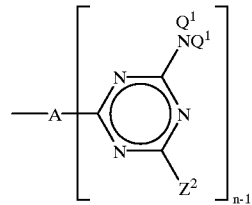

A is an n-functional anchor,
n is at least 2,
each Q$^1$ is independently selected from the group consisting of hydrogen, halogen, a hydrocarbyl and a hydrocarbyloxy hydrocarbyl, and
each Z$^2$ is independently selected from the group consisting of hydrogen, hydrocarbyl and a group represented by the formula —N(Q$^1$)$_2$, The term "hydrocarbyl," in the context of the present invention, is a group which contains carbon and hydrogen atoms and includes, for example, alkyl, aryl, aralkyl, alkenyl, and substituted derivatives thereof. Likewise, the term "hydrocarbylene" refers to a divalent hydrocarbyl such as, for example, alkylene, arylene, aralkylene, alkenylene, and substituted derivatives thereof.

The group A in the above formula is an n-functional anchor which can, for example, be a hydrocarbyl residue, an amino compound residue, oxygen or sulfur. More preferably, the (halo)amino group-containing 1,3,5-triazines including the group A have the following general formula

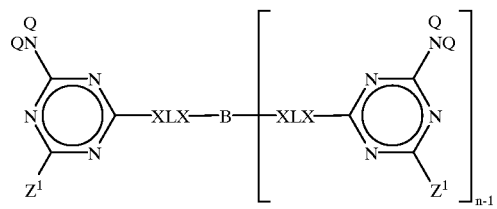

wherein B is selected from the group consisting of a hydrocarbylene and a hydrocarbyleneoxy hydrocarbyl,
each X is independently selected from the group consisting of NH,
N(hydrocarbyl), N(hydrocarbyloxy hydrocarbyl), CH$_2$, O, S, CO$_2$ and
NHCO$_2$,
each L is independently selected from the group consisting of a hydrocarbylene and a hydrocarbyleneoxy hydrocarbyl,
n is at least 2, and
Q, Q$^1$ and Z$^1$ are as defined above.

Most preferred for use in the present invention, however, are those (halo)amino group-containing 1,3,5-triazines (i) wherein both Z and Z$^1$ are represented by the formula —N(Q$^1$)$_2$ (melamines); and (ii) wherein Z$^1$ is hydrogen or a hydrocarbyl, and Z is represented by the formula —N(Q$^1$)$_2$ (guanamines).

The preferred melamines are those wherein each Q$^1$ is independently selected from hydrogen and halogen, more preferably hydrogen and chlorine. As specific preferred examples may be mentioned melamine (Q and Q$^1$ are all hydrogen), N,N',N"-trichloromelamine (one of the Q groups is hydrogen and the other is chlorine, and one Q$^1$ group on each of the remaining nitrogens is hydrogen while the other is chlorine), and hexachloromelamine (Q and Q$^1$ are all chlorine).

The preferred guanamines are those represented by the above general formula wherein Z$^1$ is more preferably selected from the group consisting of an alkyl of 1 to 20 carbon atoms, alkenyl of 3 to 20 carbon atoms, aryl of 6 to 20 carbon atoms, and aralkyl of 7 to 20 carbon atoms; and each Q$^1$ is independently selected from hydrogen and halogen, more preferably hydrogen and chlorine. As specific preferred examples may be mentioned acetoguanamine, ethylcarboguanamine, cyclohexylcarboguanamine, benzoguanamine, the N,N'-dichloro derivatives thereof, and N,N,N',N'-tetrachloro derivatives thereof.

Carbon Monoxide

The carbon monoxide which can be employed in the present invention may be pure carbon monoxide or may contain other gases such as, for example, nitrogen, argon, helium, carbon dioxide, a hydrocarbon or a halogenated hydrocarbon. Generally, any commercially available carbon monoxide may be utilized; however, it is preferred that the carbon monoxide be substantially free of water for the reasons discussed further below.

The Metal Catalyst System

Any metal catalyst system containing a metal promoter capable of promoting carbonylation of the (halo)amino groups of the 1,3,5-triazine is usable in the process of the present invention. Preferably, the metal promoter is a group VII or group I-B metal or a compound containing a group VII or group I-B metal, including mixtures and complexes thereof, such as disclosed in a number of the previously incorporated references. More preferably, the metal promoter is a compound containing a metal selected from the group consisting of copper, palladium, platinum, ruthenium, rhodium and mixtures thereof, and especially the oxides, halides and organic acid salts of these metals. Most preferred for use in the present invention are copper (0), palladium (0) and palladium compounds selected from the group consisting of palladium (II) chloride, palladium (II) bromide, palladium (II) acetate, palladium (II) acetyl acetonate, palladium (II) oxide, and mixtures thereof.

To promote solubility, the metal catalyst system may comprise a complex of the metal promoter with one or more ligands. In such cases, either the complex is first prepared and thereafter added to the reaction mixture or, alternatively, it is prepared in situ by addition of an uncomplexed metal compound and one or more ligands to the reaction mixture to form a complex thereof prior to carbonylation. Ligands commonly used to complex metals are suitable for use in this manner and include, for example, nitrile group containing ligands and carbon monoxide. When the ligand used is a nitrile group containing compound, it may be used as the reaction medium. Preferably the reaction medium in this case is a solvent for the ingredients of the mixture, and preferably a nitrile solvent selected from the group consisting of acetonitrile, propionitrile, butyronitrile, valeronitrile, benzyl nitrile, benzonitrile, and mixtures thereof.

The Oxidant System

When an amino group or a mixed haloamino group is to be carbonylated, it has been found that relatively large amounts of the metal promoter are required to produce high yields of the isocyanate or carbamate functional 1,3,5-triazines. Without being bound by any theory, it is believed that the metal promoter is somehow reduced under carbonylation conditions rendering it catalytically inactive.

When an oxidant system is additionally present during carbonylation along with the metal promoter, however, the amount of the metal promoter required to produce high yields is dramatically reduced to normal catalytic levels. Any oxidant system capable of restoring the metal promotor to a promotively effective oxidation state is usable in the present invention as the oxidant system. The oxidant system typically comprises an ingredient or a plurality of ingredients capable of accepting an electron from the metal promoter, thereby restoring it to a promotively effective oxidation state for carrying out the carbonylation reaction. Without being bound by any theory or structure, it is believed that the presence of an oxidant system regenerates the promotively effective state of the metal promoter, thus enabling the regenerated species to promote the carbonylation reaction through a multiplicity of cycles, referred to herein as "turnovers."

The preferred oxidant system is selected from the group consisting of a copper (II) salt, an alkali metal iodide/oxygen couple, molecular oxygen, hydroquinones, dialkyl peroxides and other compounds containing reducible oxygen, including mixtures of the above.

The Hydrogen Halide Acceptor

When a mixed haloamino group or a fully haloamino group is to be carbonylated, hydrogen halides are produced as by-products of the carbonylation. The presence of hydrogen halides, however, is undesirable due to their noxious and corrosive nature. In such instances, it is preferred to conduct the reaction in the presence of a hydrogen halide acceptor, more preferably weak organic or inorganic bases such as, for example, alkali metal phosphates, alkaline earth metal phosphates, alkali metal carboxylates and alkali metal carbonates. Especially preferred hydrogen halide acceptors include calcium phosphate, potassium hydrogen phosphate, sodium phosphate dibasic, sodium acetate and potassium acetate.

The Hydroxy Compound

As mentioned earlier, carbamate functional 1,3,5-triazine derivatives can readily be produced in accordance with the present invention by one of two routes—(i) reacting the above-described components in the presence of a hydroxy compound, or (ii) by post-reacting the isocyanate 1,3,5-triazine derivative with such hydroxy compound.

A wide variety of hydroxy compounds are suitable for use in forming carbamates, and are described in detailed in the previously incorporated references. As preferred examples may be mentioned alcohols and phenols.

As suitable alcohols may be mentioned, for example, straight or branched monohydric or polyhydric alkanols and alkenols having 1 to 20 carbon atoms per molecule, monohydric or polyhydric cycloalkanols and cycloalkenols having 3 to 20 carbon atoms in the molecule, and monohydric and polyhydric aralalkyls having 7 to 20 carbon atoms per molecule. Further, these alcohols may also have a substituent such as a halogen atom, a cyano group, an alkoxy group, a sulfoxide group, a sulfone group, a carbonyl group, an ester group, an ether group and an amide group. Mixtures of the above are also suitable.

As preferred alcohols may be mentioned aliphatic linear, cyclic, saturated, or unsaturated alcohols having 1 to 8 carbon atoms, as well as mixtures thereof. As specific preferred examples may be mentioned methanol, ethanol, 1-propanol, 2-propanol, 1-butanol, 2-butanol, iso-butanol, tert-butanol, pentanol, hexanol, cyclohexanol, heptanol, octanol, ethylhexyl alcohol, benzyl alcohol, allyl alcohol, ethylene chlorohydrin, ethylene glycol, propylene glycol, 1,3-propanediol, 1,4-butanediol, ethoxyethanol, hydroxyethoxyethanol, 1-methoxy-2-propanol and mixtures thereof.

As suitable phenols may be mentioned phenol, various alkyl phenols, various alkoxy phenols, various halogenated phenols, dihydroxybenzene, 4,4-dihydroxydiphenylmethane, various bisphenols such as bisphenol-A, and hydroxynaphthalenes. As specific preferred examples may be mentioned phenol, 2-methyl phenol, 3-methyl phenol, 4-methyl phenol, 2-chlorophenol, 3-chlorophenol, 4-chlorophenol, catechol, resorcinol, hydroquinone, and mixtures thereof.

Carbonylation Conditions

In the practice of the invention, the components of the reaction mixture are contacted at a temperature, carbon monoxide pressure, and length of time sufficient to carbonylate at least a portion of the (halo)amino groups of the 1,3,5-triazine.

The carbonylation temperature may vary widely, but is typically in the range of from about 20° C. to about 1 80° C.

The carbonylation pressure may also vary widely, but is typically in the range of from atmospheric to about 1400 psig, with pressures of from about 700 psig to about 1100 psig being preferred. The actual carbon monoxide pressure may be slightly lower due to the presence of gaseous inerts in the carbon monoxide stream.

The length of time for carbonylation again may vary widely, but is typically in the range of from about 2 hours to about 96 hours.

The metal catalyst system is preferably utilized in catalytic amounts, typically ranging from about 0.01 to about 10 mole % metal promoter, and preferably from about 0.1 to about 3 mole % metal promoter, based upon the number of moles of (halo)amino groups in the 1,3,5-triazines to be carbonylated.

The oxidant system, when required, is preferably present in a sufficient amount to promote the carbonylation of the amino and mixed haloamino groups. Typically, the oxidant system will be present in an at least stoichiometric amount based upon the number of H atoms present in the amino and mixed haloamino groups.

The hydrogen halide acceptor, when required, is preferably present in an amount to substantially fully neutralize any hydrogen halide by-product from the carbonylation of the mixed and fully haloamino groups of the 1,3,5-triazines.

The carbonylation is preferably conducted in the presence of solvents such as, for example, aromatic hydrocarbons such as benzene, toluene, xylene and mesitylene; nitriles such as acetonitrile, propionitrile, butyronitrile, valeronitrile, benzyl nitrile and benzonitrile; sulfones such as sulforane, methylsulforane and dimethylsulforane; ethers such as tetrahydrofuran, 1,4-dioxane, 1,2-dimethoxyethane, glyme, diglyme and triglyme; ketones such as acetone and methyl ethyl ketone; esters such as ethyl acetate and ethyl benzoate; amides such as N,N-dimethylformamide, N,N-dimethylacetamide, N-methylpyrrolidone and hexamethylphosphoramide; and a variety of hydroxy compounds suhc as the lower alkanols. Some of these solvents, however, may be incompatible when haloamino-1,3,5-triazines are carbonylated due to their potential reactivity with such haloamino-1,3,5-triazines, and should be avoided under conidtions where such reactivity may become a concern. The preferred solvents are the nitriles and hydroxy compounds.

As discussed above, if carbamate functional 1,3,5-triazines are desired, the carbonylation may be carried out in the presence of a hydroxy compound (both a reactant and solvent), or the hydroxy compound may be added subsequent to the carbonylation. The amount of hydroxy compound added, of course, will vary depending upon the desired degree of carbamate formation. Typically, for full conversion to carbamate functionality, a stoichiometric excess (based upon isocyanate formation) should be utilized. To promote formation of the carbamate functionality, a well-known urethanation catalyst may also be added.

When carbamate functional products are desired, it is preferred to conduct the reaction in the present of an alcohol/cosolvent system. The alcohol/cosolvent ratio can vary widely, but generally should be in the range of about 2/1 to about 10/1. The preferred cosolvent is a nitrile solvent.

In addition, it is preferred to conduct the carbonylation in the substantial absence of water, as the presence of water may cause side reactions such as the hydrolysis of isocyanates and carbamates, and the water gas reaction of carbon monoxide. To avoid these problems, therefore, it may be desired to conduct the carbonylation in the presence of a dehydrating additive such as, for example, zeolites, orthoesters, ketals, acetals, enolethers and trialkyl orthoborates.

The invention will now be illustrated by reference to the following examples:

EXAMPLE 1

Carbonylation of Melamine in the Presence of 1-Butanol with a $Pd(II)Cl_2/Cu(II)Cl_2$ Catalyst System Preparation of N-Butoxycarbonylamino-1,3,5-Triazines Melamine was contacted with carbon monoxide at 800 psig, and at ca. 100° C. for 24 hours, in 4:1 1-butanol/acetonitrile. The reaction was run under oxygen free conditions. A catalytic quantity of $Pd(II)Cl_2$ was used with $Cu(II)Cl_2$ as a cocatalyst.

A glass-lined, two-liter, stainless steel Zipperclave was charged with the following:

120 cc of acetonitrile, $Pd(II)Cl_2$ (0.32 g), 480 cc of 1-butanol, $CU(II)Cl_2$(24.20 g), sodium phosphate, dibasic (25.48 g), and melamine (7.58 g).

The reactor and reaction mixture were purged with nitrogen. The reactor was pressurized to 600 psig with carbon monoxide at room temperature. The reactor temperature was brought to ca. 100° C., and the system was further pressurized to 800 psig with carbon monoxide. The reaction mixture was stirred under these conditions for 24 hours. The reactor was cooled to room temperature, and the carbon monoxide pressure vented. Nitrogen purge cycles were used to remove dissolved carbon monoxide from the reaction mixture.

Approximately one-half of the product (183.42 g) was charged to a filtration funnel containing celite covered with a layer of silica gel. The dried product, (6.77 g) containing the N-butoxycarbonylamino-1,3,5-triazines, was obtained by removing the 1-butanol/acetonitrile from the filtrate under reduced pressure. A catalytic turnover number (TON) of 7.7 (mol butoxycarbonylamino groups/mol palladium) was determined from $^1$H-NMR, and mass spectroanalysis of the isolated product.

EXAMPLE 2

Carbonylation of Melamine in the Presence of 1-Butanol and Pd(0) Preparation of N-Butoxycarbonylamino-1,3,5-Triazines Melamine was contacted with carbon monoxide at 170° C., in 1-butanol, and in the presence of a catalytic quantity of Pd(0) and sodium iodide. A quantity of oxygen in 20% excess over stoichiometric (on amino groups) was present.

A glass-lined, two-liter, stainless steel Zipperclave was charged with the following:

600 cc of 1-butanol,

Pd(0) catalyst (3N5 powder, 60 mesh; 0.1921 g), sodium iodide (2.7063 g), and the melamine (7.5810 g).

The reactor and reaction mixture were purged with nitrogen. The reactor was pressurized to 500 psig with carbon monoxide at room temperature. Air was charged to the reactor to a total pressure of 630 psig. The reaction temperature was brought to ca. 170° C., and the system was further pressurized to 1000 psig with carbon monoxide. The reactor was stirred under these conditions for ca. 2 hours reaction time at that temperature. The reactor was cooled to room temperature, and the carbon monoxide pressure vented. Nitrogen purge cycles were used to remove dissolved carbon monoxide from the reaction mixture.

A portion of the neat reaction mixture (212.3 g) was charged to a filtration funnel containing celite covered with a layer of silica gel. The dried product (3.92 g), containing the N-butoxycarbonylamino-1,3,5-triazine, was obtained by removing 1-butanol from the filtrate under reduced pressure. A catalytic turnover number (TON) of 7.4 (mol butoxycarbonylamino groups/mol palladium) was determined from $^1$H-NMR and mass spectroanalysis of the isolated product.

EXAMPLE 3

Carbonylation of N,N',N"-Trichloromelamine in the Presence of 1-Butanol and Mixed Pd(0)/Pd(II)Cl$_2$ Catalyst Preparation of N-Butoxycarbonylamino-1,3,5-Triazines Trichloromelamine was reacted with carbon monoxide in the presence of 1-butanol at ca. 30° C. for 18 hours using a catalytic quantity of an equimolar mixture of Pd(0) and PdCl$_2$ (at 1.5 mol % Pd on amino groups).

A glass-lined, two-liter, stainless steel Zipperclave was charged with the following:

acetonitrile (120 cc),

PdCl$_2$ (0.2402 g),

Pd(0) (3N5 powder, 60 mesh; 0.1456 g), 1-butanol (480 cc), sodium phosphate, dibasic (25.48 g), and trichloromelamine (13.78 g).

The reactor and reaction mixture were purged with nitrogen. The reactor was pressurized to 800 psig with carbon monoxide. The system was stirred at ambient temperature for ca. 18 hrs. The carbon monoxide pressure was vented, and purge cycles using nitrogen were used to remove dissolved carbon monoxide from the reaction mixture.

A portion (255.5 g) of the neat reaction product mixture was passed through a silica gel/celite filter bed. The dried product (9.68 g), containing the N-butoxycarbonylamino-1,3,5-triazine, was obtained by removing 1-butanol/acetonitrile from the filtrate under reduced pressure. A catalytic turnover number (TON) of 8.2 (mol butoxycarbonylamino groups/mol palladium) was determined from $^1$H-NMR and mass spectroanalysis of the isolated product.

EXAMPLE 4

Carbonylation of Cyclohexylguanamine in the Presence of 1-Butanol and Pd(0) Preparation of N-Butoxycarbonylamino-6-cyclohexyl-1,3,5-Triazines Cyclohexylguanamine was contacted with carbon monoxide in the presence of 1-butanol at 170° C., and in the presence of a catalytic quantity of Pd(0) and sodium iodide. A quantity of oxygen in 20% excess over stoichiometric (on amino groups) was present.

A glass-lined, two-liter, stainless steel Zipperclave was charged with the following:

1-butanol (600 cc),

Pd(0) (3N5 powder, 60 mesh; 0.1922 g), sodium iodide (2.6957 g), and cyclohexyl guanamine (11.60 g).

The reactor and reaction mixture were purged using nitrogen. The reactor was pressurized to 500 psig with carbon monoxide. Air was charged to the reactor to a total pressure of 630 psig. The reaction temperature was brought to ca. 170° C., and the system was pressurized to a final pressure of 1000 psig with carbon monoxide. The system was stirred under carbon monoxide for ca. 2 hours at 170° C., followed by stirring an additional 60 hours at ambient temperature. Nitrogen purge cycles were used to remove dissolved carbon monoxide from the reaction mixture.

A portion of the neat reaction mixture (250.4 g) was charged to a filtration funnel containing celite covered with a layer of silica gel. The dried product (13.10 g), containing the N-butoxycarbonylamino-6-cyclohexyl-1,3,5-triazine, was obtained by removing 1-butanol from the filtrate under reduced pressure. A catalytic turnover number (TON) of 12.5 (mol butoxycarbonylamino groups/mol palladium) was determined from $^1$H-NMR and mass spectroanalysis of the isolated product.

EXAMPLE 5

Carbonylation of N,N',N'-Trichlorobenzoguanamine in the Presence of 1-Butanol and a Ru$_3$(CO)$_{12}$ Catalyst Preparation of N-Butoxycarbonylamino-6-phenyl-1,3,5-Triazines N,N,N-Trichlorobenzoguanamine was reacted with carbon monoxide in the presence of 1-butanol at 90° C., and in the presence of a catalytic quantity of Ru$_3$(CO)$_{12}$.

A glass-lined, two-liter, stainless steel Zipperclave was charged with the following:

1-butanol (300 cc),

Ru$_3$(CO)$_{12}$ (0.0395 g), and

N,N',N'-trichlorobenzoguanamine (1.7274 g).

The reactor and reaction mixture were purged using nitrogen. The reactor was pressurized to 800 psig with carbon monoxide. The reaction temperature was brought to ca. 90° C., and the system was pressurized to a final pressure of 1000 psig with carbon monoxide. The system was stirred under carbon monoxide for ca. 18 hours at 90° C., followed by stirring an additional 3 hours at ambient temperature. Nitrogen purge cycles were used to remove dissolved carbon monoxide from the reaction mixture.

The neat reaction mixture (83.0 g) was charged to a filtration funnel containing celite covered with a layer of silica gel. The dried product (2.83 g), containing the N-butoxycarbonylamino-6-phenyl-1,3,5-triazine, was obtained by removing 1-butanol from the filtrate under reduced pressure. A catalytic turnover number (TON) of 20.3 (mol butoxycarbonylamino groups/mol ruthenium) was determined from $^1$H-NMR and mass spectroanalysis of the isolated product.

EXAMPLE 6

Carbonylation of Benzoguanamine in the Presence of Methanol and Pd(II)Cl$_2$ Preparation of N-Methoxycarbonylamino-6-Phenyl-1,3,5-Triazines A mixture of benzoguanamine (1.9 g), methanol (60 ml), acetonitrile (15 ml), and palladium chloride (3.50 g) was charged to a 300 ml capacity Parr reactor. The reactor was flushed with nitrogen and pressurized with carbon monoxide to 880 psig. The reaction mixture was stirred at room temperature for 26 hours. The reactor was vented of carbon monoxide, flushed with nitrogen and the contents were filtered through Celite.

Concentration of the filtrate under reduced pressure afforded a green solid (1.7 g). Analysis of the product by Thin Layer Chromatography (TLC) and Mass Spectroscopy (MS) evidenced that 2-methoxycarbonylamino-4-amino-6-phenyl-1,3,5-triazine had been formed.

EXAMPLE 7

Carbonylation of N,N',N'-Trichlorobenzoguanamine in the Presence of Methanol and Pd(II)Cl$_2$ Preparation of N-Methoxycarbonylamino-6-Phenyl-1,3,5-Triazines A mixture of N,N,N'-trichlorobenzoguanamine (2.9 g), methanol (60 ml), acetonitrile (15 ml), and palladium chloride (2.70 g) was charged to a 300 ml capacity Parr reactor. The reactor was flushed with nitrogen and pressurized with carbon monoxide to 850 psig. The reaction mixture was stirred at room temperature for 46 hours. The reactor was vented of carbon monoxide, flushed with nitrogen and the contents were filtered through Celite. Concentration of the filtrate under reduced pressure afforded a tan solid (3.8 g). Analysis of the product by TLC and MS evidenced that both the 2,4-di(methoxycarbonylamino)-6-phenyl-1,3,5-triazine and the 2-methoxycarbonylamino-4-amino-6-phenyl-1,3,5-triazine had been formed.

EXAMPLE 8

Carbonylation of N-Hexachloromelamine in the Presence of Methanol and Pd(II)Cl$_2$ Preparation of N-Methoxycarbonylamino-1,3,5-Triazines A mixture of hexachloromelamine (3.3 g), methanol (60 ml), acetonitrile (15 ml), and palladium chloride (3.5 g) was charged to 300 ml capacity Parr reactor. The reactor was flushed with nitrogen and pressurized with carbon monoxide at 900 psig. The reaction mixture was stirred at room temperature for 25 hours. The reactor was vented of carbon monoxide, flushed with nitrogen and the contents were filtered through Celite and a thin layer of silica gel. Concentration of the filtrate under reduced pressure afforded a brown solid (8.0 g). Analysis by TLC and MS evidenced that the isolated product contained the tris-, bis- and mono-substituted N-methoxycarbonylamino-1,3,5-triazines.

EXAMPLE 9

Carbonylation of N-Hexachloromelamine in the Presence of Butanol and Pd(II)Cl$_2$ Preparation of N-Butoxycarbonylamino-1,3,5-Triazines A mixture of hexachloromelamine (3.3 g), potassium hydrogen phosphate (6.1 g), n-butanol (58 ml), acetonitrile (18 ml), and palladium chloride (5.3 g) was charged to a 300 ml capacity Parr reactor. The reactor was flushed with nitrogen and pressurized with carbon monoxide at 900 psig. The reaction mixture was stirred at room temperature for 25 hours and then heated to 60° C. for an additional 24 hours. The reactor was cooled, vented of carbon monoxide, and flushed with nitrogen. The contents were then filtered through Celite and a thin layer of silica gel. Concentration of the filtrate under reduced pressure afforded a dark solid (4.9 g). Analysis by TLC and MS evidenced that the isolated product contained the tris-, bis- and mono-substituted N-butoxycarbonylamino-1,3,5-triazines.

EXAMPLE 10

Carbonylation of N,N'N"-Trichloromelamine in the Presence of Methanol and Pd(II)Cl$_2$ Preparation of N-Methoxycarbonylamino-1,3,5-Triazines A mixture of N,N',N"-trichloromelamine (2.3 g), sodium acetate (1.2 g), methanol (60 ml), acetonitrile (15 ml), and palladium chloride (2.7 g) was charged to a 300 ml capacity Parr reactor. The reactor was flushed with nitrogen and pressurized with carbon monoxide to 700 psig. The reaction mixture was stirred at room temperature for 44 hours. The reactor was vented of carbon monoxide, flushed with nitrogen and the contents were filtered through Celite. Concentration of the filtrate under reduced pressure afforded a tan solid (4.0 g). Analysis by TLC and MS evidenced that the isolated product contained the tris-, bis- and mono-substituted N-methoxycarbonylamino-1,3,5-triazines.

EXAMPLE 11

Carbonylation of N,N'N"-trichloromelamine in the Presence of Butanol and Pd(II)Cl$_2$ Preparation of N-Butoxycarbonylamino-1,3,5-Triazines A mixture of N,N'N"-trichloromelamine (2.3 g), sodium acetate (1.9 g), n-butanol (60 ml), acetonitrile (15 ml), and palladium chloride (4.0 g) was charged to a 300 ml capacity Parr reactor. The reactor was flushed with nitrogen and pressurized with carbon monoxide to 980 psig. The reaction mixture was stirred at room temperature for 24 hours and heated to 60° C. for an additional 24 hours. The reactor was cooled, vented of carbon monoxide, and flushed with nitrogen. The contents were then filtered through Celite and a thin layer of silica gel. Concentration of the filtrate under reduced pressure afforded a green solid (4.3 g) product which contained the tris-, bis- and mono-substituted N-butoxycarbonylamino-1,3,5-triazines.

EXAMPLE 12

Carbonylation of N,N',N"-Trichloromelamine in the Presence of Butanol With a Palladium/Copper Cocatalyst System Preparation of N-Butoxycarbonylamino-1,3,5-Triazines A mixture of N,N',N"-trichloromelamine (2.3 g), potassium hydrogen phosphate (6.1 g), butanol (45 ml), acetonitrile (30 ml), palladium chloride (0.5 g), and cupric chloride (6.0 g) was charged to a 300 ml capacity Parr reactor. The reactor was flushed with nitrogen and pressurized with carbon monoxide to 820 psig. The reaction mixture was stirred at room temperature for 24 hours and heated to 60° C. for an additional 23 hours. The reactor was cooled, vented of carbon monoxide, and flushed with nitrogen. The contents were then filtered through Celite and a thin layer of silica gel. Concentration of the filtrate under reduced pressure afforded a dark solid (8.3 g). Analysis by TLC and MS evidenced that the isolated product was similar in nature to that obtained in Example 11.

EXAMPLE 13

Carbonylation of Melamine in the Presence of Methanol and Pd(II)Cl$_2$ Preparation of N-Methoxycarbonylamino-1,3,5-Triazines A mixture of melamine (1.3 g), potassium hydrogen phosphate (6.1 g), methanol (80 ml), acetonitrile (20 ml), and palladium chloride (5.3 g) was charged to a 300 ml capacity Parr reactor. The reactor was flushed with nitrogen and pressurized with carbon monoxide to 880 psig. The reaction mixture was stirred at room temperature for 24 hours and heated to 69° C. for 44 hours. The reactor was cooled, vented of carbon monoxide, and flushed with nitrogen. The contents were filtered through Celite and a thin layer of silica gel. Concentration of the filtrate under reduced pressure afforded a light green solid (4.6 g). Analysis by TLC and MS evidenced that the isolated product contained the bis- and mono-substituted N-methoxycarbonylamino-1,3,5-triazines.

EXAMPLE 14

Carbonylation of Melamine in the Presence of Butanol and Pd(II)Cl$_2$ Preparation of N-Butoxycarbonylamino-1,3,5-Triazines A mixture of melamine (1.3 g), potassium hydrogen phosphate (6.1 g), n-butanol (80 ml), acetonitrile (20 ml), and palladium chloride (5.3 g) was charged to a 300 ml capacity Parr reactor. The reactor was flushed with nitrogen and pressurized with carbon monoxide to 950 psig. The reaction mixture was stirred at 90° C. for 74 hours. The reactor was cooled, vented of carbon monoxide, and flushed with nitrogen. The contents were filtered through Celite and a thin layer of silica gel. Concentration of the filtrate under reduced pressure afforded a brown solid (2.0 g). Analysis by TLC and MS evidenced that the isolated product contained the tris-, bis- and mono-substituted N-butoxycarbonylamino-1,3,5-triazines.

EXAMPLE 15

Carbonylation of Melamine in the Presence of 1-Butanol and Cu(0) Preparation of N-Butoxycarbonylamino-1,3,5-Triazines Melamine was reacted with carbon monoxide in the presence of 1-butanol at 150° C., and in the presence of a catalytic quantity of Cu(0) and potassium iodide. A quantity of oxygen in 20% excess over stoichiometric (on amino groups) was present.

A glass-lined, two-liter, stainless steel Zipperclave was charged with the following:

1-butanol (600 cc),

Cu(0) (powder, 150 mesh; 0.1150 g), potassium iodide (2.9988 g), and melamine (7.5849 g).

The reactor and reaction mixture were purged using nitrogen. The reactor was pressurized to 500 psig with carbon monoxide. Air was charged to the reactor to a total pressure of 630 psig. The reaction temperature was brought to ca. 150° C., followed by stirring an additional 15 hours at ambient temperature. Nitrogen purge cycles were used to remove dissolved carbon monoxide from the reaction mixture.

A portion of the neat reaction mixture (247.3 g) was charged to a filtration funnel containing celite covered with a layer of silica gel. The dried product (2.93 g), containing the N-butoxycarbonylamino-1,3,5-triazines, was obtained by removing 1-butanol from the filtrate under reduced pressure. A catalytic turnover number (TON) of 2.9 (mol butoxycarbonylamino groups/mol copper) was determined from $^1$H-NMR of the isolated product.

Although the present invention, is described with reference to certain preferred embodiments, it is apparent that modifications and variations thereof may be made by those skilled in the art without departing from the scope of this invention as defined by the appended claims.

We claim:

1. A process for preparing carbonylated derivatives of (halo)amino-1,3,5-triazines, comprising the step of contacting:

(a) a (halo)amino group-containing 1,3,5-triazine represented by the formula:

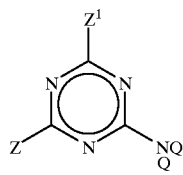

wherein each Q is independently selected from the group consisting of hydrogen and halogen, Z is selected from the group consisting of a group represented by the formula —N(Q$^1$)$_2$, and a group represented by the formula:

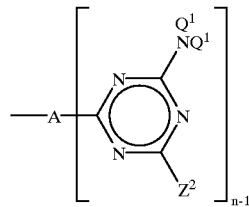

Z$^1$ is selected from the group consisting of hydrogen, hydrocarbyl, a group represented by the formula —N(Q$^1$)$_2$, and a group represented by the formula:

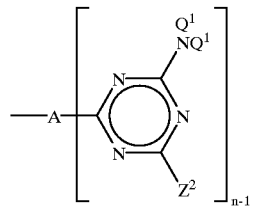

A is an n-functional anchor, n is at least 2, each Q$^1$ is independently selected from the group consisting of hydrogen, halogen, a hydrocarbyl and a hydrocarbyloxy hydrocarbyl, and each Z$^2$ is independently selected from the group consisting of hydrogen, hydrocarbyl and a group represented by the formula —N(Q$^1$)$_2$;

(b) carbon monoxide; and (c) a metal catalyst system containing a metal promoter for promoting carbonylation;

at a temperature, carbon monoxide pressure, and length of time sufficient to carbonylate at least a portion of the (halo)amino groups of the 1,3,5-triazine.

2. The process of claim 1, wherein Z is N(Q$^1$)$_2$.

3. The process of claim 2, wherein Z$^1$ is N(Q$^1$)$_2$.

4. The process of claim 3, wherein each Q$^1$ is independently selected from the group consisting of hydrogen and halogen.

5. The process of claim 2, wherein Z$^1$ is selected from the group consisting of hydrogen and a hydrocarbyl.

6. The process of claim 5, wherein each Q$^1$ is independently selected from the group consisting of hydrogen and halogen.

7. The process of claim 1, wherein Z$^1$ is a hydrocarbyl is selected from the group consisting of an alkyl of 1 to 20 carbon atoms, an alkenyl of 3 to 20 carbon atoms, an aryl of 6 to 20 carbon atoms, and an aralkyl of 7 to 20 carbon atoms.

8. The process of claim 1, wherein the metal catalyst system contains a metal promoter selected from the group consisting of a group VIII metal, a group I-B metal, a compound containing a group VIII metal, a compound containing a group I-B metal, and mixtures thereof.

9. The process of claim 8, wherein the metal promoter is selected from the group consisting of copper, palladium, platinum, ruthenium, rhodium, compounds thereof, and mixtures of any of the foregoing.

10. The process of claim 9, wherein the metal promoter is selected from the group consisting of copper (0), palladium (0), palladium (II) chloride, palladium (II) bromide, palladium (II) acetate, palladium (II) acetyl acetonate, palladium (II) oxide, and mixtures thereof.

11. The process of claim 1, wherein (a), (b) and (c) are contacted in the presence of an oxidant system.

12. The process of claim 11, wherein the oxidant system is an ingredient capable of accepting an electron from the metal promoter.

13. The process of claim 1, wherein (a), (b) and (c) are contacted in the presence of a hydrogen halide acceptor.

14. The process of claim 13, wherein the hydrogen halide acceptor is a weak base.

15. The process of claim 1, wherein (a), (b) and (c) are contacted in the presence of a hydroxy compound.

16. The process of claim 1, wherein (a), (b) and (c) are contacted in the presence of a solvent.

17. The process of claim 16, wherein the solvent comprises a nitrile solvent.

18. The process of claim 17, wherein the solvent comprises a combination of a nitrile solvent with a hydroxy compound.

19. A process for preparing carbamate functional derivatives of (halo)amino-1,3,5-triazines, comprising the step of contacting:

(a) a (halo)amino group-containing 1,3,5-triazine represented by the formula:

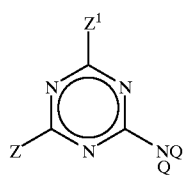

wherein each Q is independently selected from the group consisting of hydrogen and halogen, Z is selected from the group consisting of a group represented by the formula —$N(Q^1)_2$, and a group represented by the formula:

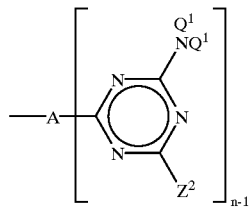

$Z^1$ is selected from the group consisting of hydrogen, hydrocarbyl, a group represented by the formula —$N(Q^1)_2$, and a group represented by the formula:

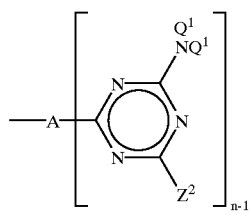

A is an n-functional anchor, n is at least 2, each $Q^1$ is independently selected from the group consisting of hydrogen, halogen, a hydrocarbyl and a hydrocarbyloxy hydrocarbyl, and each $Z^2$ is independently selected from the group consisting of hydrogen, hydrocarbyl and a group represented by the formula —$N(Q^1)_2$;

(b) carbon monoxide;

(c) a metal catalyst system containing a metal promoter for promoting carbonylation; and (d) a hydroxy compound, at a temperature, carbon monoxide pressure, and length of time sufficient to carbonylate at least a portion of the (halo)amino groups of the 1,3,5-triazine.

20. A process for preparing carbamate functional derivatives of (halo)amino-1,3,5-triazines, comprising the steps of (1) contacting:

(a) a (halo)amino group-containing 1,3,5-triazine represented by the formula:

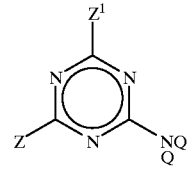

wherein each Q is independently selected from the group consisting of hydrogen and halogen, Z is selected from the group consisting of a group represented by the formula —$N(Q^1)_2$, and a group represented by the formula:

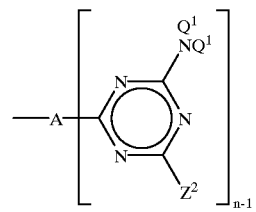

$Z^1$ is selected from the group consisting of hydrogen, hydrocarbyl, a group represented by the formula —$N(Q^1)_2$, and a group represented by the formula:

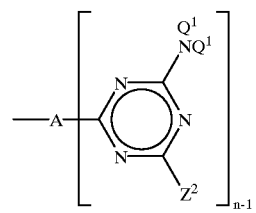

A is an n-functional anchor, n is at least 2, each $Q^1$ is independently selected from the group consisting of hydrogen, halogen, a hydrocarbyl and a hydrocarbyloxy hydrocarbyl, and each $Z^2$ is independently selected from the group consisting of hydrogen, hydrocarbyl and a group represented by the formula —$N(Q^1)_2$;

(b) carbon monoxide;

(c) a metal catalyst system containing a metal promoter for promoting carbonylation, at a temperature, carbon monoxide pressure, and length of time sufficient to carbonylate at least a portion of the (halo)amino groups of the 1,3,5-triazine, then (2) post-reacting the product of step (1) with a hydroxy compound.

21. The process of claim 1, wherein the carbonylation temperature is in the range of from about 20° C. to about 180° C., and the carbonylation pressure is in the range of from atmospheric to about 1400 psig.

22. The process of claim 19, wherein the hydroxy compound is selected from the group consisting of straight or branched monohydric or polyhydric alkanols and alkenols having 1 to 20 carbon atoms per molecule, monohydric or polyhydric cycloalkanols and cycloalkenols having 3 to 20 carbon atoms in the molecule, monohydric and polyhydric aralkyls having 7 to 20 carbon atoms per molecule, phenols and mixtures thereof.

23. The process of claim 19, wherein the carbonylation temperature is in the range of from about 20° C. to about 180° C., and the carbonylation pressure is in the range of from atmospheric to about 1400 psig.

24. The process of claim 19, wherein Z is $N(Q^1)_2$.

25. The process of claim 24, wherein $Z^1$ is $N(Q^1)_2$.

26. The process of claim 25, wherein each $Q^1$ is independently selected from the group consisting of hydrogen and halogen.

27. The process of claim 19, wherein (a), (b), (c) and (d) are contacted in the presence of an oxidant system.

28. The process of claim 19, wherein (a), (b), (c) and (d) are contacted in the presence of a hydrogen halide acceptor.

29. The process of claim 19, wherein (a), (b), (c) and (d) are contacted in the presence of a solvent.

30. The process of claim 20, wherein the hydroxy compound is selected from the group consisting of straight or branched monohydric or polyhydric alkanols and alkenols having 1 to 20 carbon atoms per molecule, monohydric or polyhydric cycloalkanols and cycloalkenols having 3 to 20 carbon atoms in the molecule, monohydric and polyhydric aralkyls having 7 to 20 carbon atoms per molecule, phenols and mixtures thereof.

31. The process of claim 20, wherein the carbonylation temperature is in the range of from about 20° C. to about 180° C., and the carbonylation pressure is in the range of from atmospheric to about 1400 psig.

32. The process of claim 20, wherein Z is $N(Q^1)_2$.

33. The process of claim 32, wherein $Z^1$ is $N(Q^1)_2$.

34. The process of claim 33, wherein each $Q^1$ is independently selected from the group consisting of hydrogen and halogen.

35. The process of claim 20, wherein (a), (b) and (c) are contacted in the presence of an oxidant system.

36. The process of claim 20, wherein (a), (b) and (c) are contacted in the presence of a hydrogen halide acceptor.

37. The process of claim 20, wherein (a), (b) and (c) are contacted in the presence of a solvent.

* * * * *